United States Patent [19]

Sharp et al.

[11] Patent Number: 5,495,101
[45] Date of Patent: Feb. 27, 1996

[54] ENHANCEMENT FOR BROADBAND OPTICAL LIMITER WITH HOLOGRAPHIC GRATING

[75] Inventors: Edward J. Sharp, Fredericksburg, Va.; Gregory J. Salamo, Fayetteville, Ark.; Gary L. Wood, Centerville, Va.; John J. Shultz, Fayetteville, Ak.

[73] Assignee: The United States of America as represented by the Secretary of the Army, Washington, D.C.

[21] Appl. No.: 352,643

[22] Filed: Dec. 9, 1994

[51] Int. Cl.$^6$ .............................. H01J 3/14; H01J 5/16; H01J 40/14
[52] U.S. Cl. .................. 250/216; 359/7; 359/15; 359/308; 250/226
[58] Field of Search ................... 250/216, 226; 359/7, 15, 300, 308, 309

[56] References Cited

U.S. PATENT DOCUMENTS 5,073,075  12/1991  Sharp et al. .................. 250/216
5,369,511  11/1994  Amos ............................. 359/15
5,449,904   9/1995  Miller et al. ................... 250/216

*Primary Examiner*—Edward P. Westin
*Assistant Examiner*—Jacqueline M. Steady
*Attorney, Agent, or Firm*—Milton W. Lee; Alain L. Bashore; Anthony T. Lane

[57] ABSTRACT

A passive broadband sensor protection and enhancement system and technique. Incident light is focused with a cylindrical lens on the optical axis into an intense light strip onto the input face of a photorefractive crystal which may include optional anti-reflection coatings on the input and output face. A broadband high reflection coating proximate to the input face reflects all radiation from approximately 0.68 out to at least 1.5 micrometers wavelength and light exiting includes a transmitted beam and beam fan. A weak holographic grating is used to seed the beam fan, such that is fanned out of the optical path in a direction determined by the c-axis, dominant electro-optic coefficient, and charge carriers participating in the photorefractive process. The transmitted beam contains only incoherent radiation as input to a sensitive detector resulting in broadband multiline protection from the visible spectrum for substantially all pulsewidths and cw lasers, with enhanced time response and interaction length.

4 Claims, 5 Drawing Sheets

ENHANCEMENT FOR BROADBAND OPTICAL LIMITER WITH HOLOGRAPHIC GRATING

BACKGROUND OF THE INVENTION

1. Field of the Invention

The present invention generally relates to optical limiter enhancements and more specifically, to performance enhancement systems and techniques fox photorefractive crystal optical limiters.

2. Description of Prior Art

Photorefractive crystals as power limiters continue to have performance problems with regards to time response and beam depletion. The time response for photorefractive beam fanning depends inversely on the incident intensity which determines the limiting threshold. When the time response is optimized there is a proportional decrease in the limiting threshold. If ample time is allowed for the limiting to occur even very weak cw (continuous wave) beams (approx. 1 milliwatt) can be limited. The particular photorefractive process of asymmetric self-defocusing or "beam fanning" which results from wave mixing or beam coupling has been exploited as a sensor protection device. The photorefractive process arises from the: second-order non-linear optical susceptibility and has a distinguishing feature, in that the time response depends on the intensity. Improvement in the time response depends on the incident intensity (I) according to the relationship:

$$\tau = A/I^x$$

where:

x is approximately unity, and
A is a material parameter with units of energy density.
Since x is approximately unity, the material parameter A determines the limiting threshold. An example of photorefractive crystal power limiters may be found in U.S. Pat. No. 5,073,705 to Sharp et al. entitled "Broadband, Multi-line, Optical Power Limiting Scheme" issued 17 Dec. 1991, incorporated herein by reference.

While the prior art has reported using optical limiters based on photorefractive limiters none have established a basis for a specific apparatus that is dedicated to the task of resolving the particular problem at hand. What is needed in this instance is a beam fanning limiter system and technique which achieves improved time response and maximum interaction length. This would yield truly passive broadband sensor protection against high intensity, short-pulse, high repetition rate multi-line lasers and multi-line cw lasers.

SUMMARY OF THE INVENTION

It is therefore the object of the invention to provide a beam fanning limiter system and technique which achieves improved time response and maximum interaction length which yields broadband protection for all pulsewidths and cw lasers with high laser damage threshold.

According to the invention, a passive broadband sensor protection and enhancement technique and system achieves broadband multiline protection from the visible spectrum for substantially all pulsewidths and cw lasers, and also resulting in enhanced time response and interaction length. A photorefractive crystal on the optical axis is provided, where the crystal includes an input and output face. The inhibition of reflection on the input and output face of the photorefractive crystal is provided with anti-reflection coatings. A broadband high reflection coating on the anti-reflection coating of the input face provides for high reflection of broadband emission input. Incident light is focused on the optical axis into an intense light strip coincident upon the input face relative to a plane normally referred to as the c-axis of the crystal.

Light exiting from the output face of the crystal results from a photorefractive process that includes a transmitted beam and beam fan. A weak holographic grating is used to seed the beam fan by instantaneously supplying a multiplicity of weak beams which cross the input beam at an optimum angle for two beam coupling for the particular crystal being used. The beam fan is fanned out of the optical path in a direction determined by the c-axis, dominant electro-optic coefficient, and charge carriers participating in the photorefractive process. The transmitted beam contains only incoherent radiation as input to the sensitive detector resulting in broadband multiline protection from the visible spectrum for substantially all pulsewidths and cw lasers, and also resulting in enhanced time response and interaction length.

BRIEF DESCRIPTION OF THE DRAWING

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
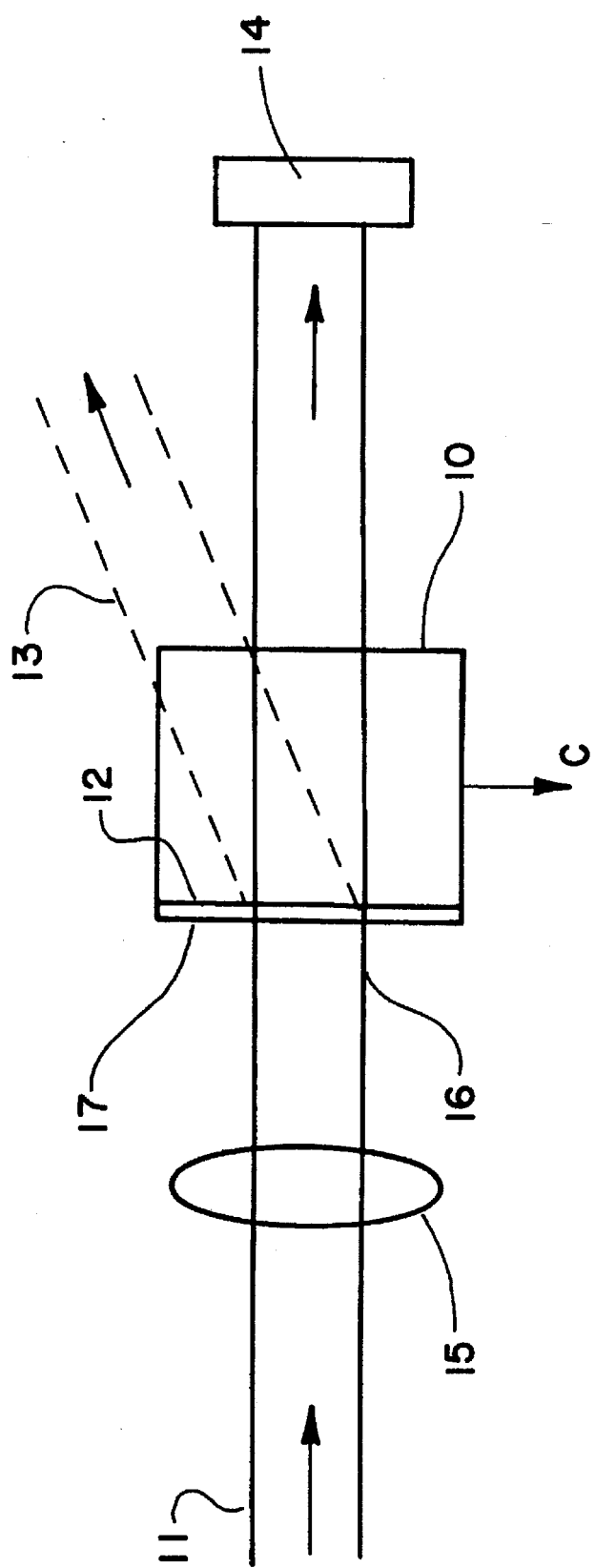
FIG. 1 is a top view of the beam pathways achieved by the present invention in a photorefractive crystal.

Referring now to the drawings, and more particularly to FIG. 1 there is shown the beam patchways generated by beam fanning in a photorefractive crystal utilizing the present invention. Photorefractive crystal 10 is arranged so that beam 11, which is coherent laser light and information containing incoherent light are incident upon crystal input face 12 which is then photorefractively "fanned" resulting in beam fan 13 as the amplified output to one side of the incident beam direction. Detector 14 then detects the incoherent light and the deamplified coherent light. The invention of related U.S. Pat. No. entitled "Fast Broadband Optical Limiter Technique and System" by Mary J. Miller et. al., which is incorporated herein by reference and assigned to the common assignee, has disclosed therewithin a novel way to maximize coupling of energy into the fanned beams and out of the incident beams. The Miller et. al. invention seeks to exploit the coherent beam amplification and deamplification process associated with beam fanning by improving the time response and by maximizing the gain-length product in any particular crystal through the use of cylindrical optics 15 which focuses input beam 11 as focused input beam 16. The present invention utilizes an additional grating 17 which provides a more improved time response as compared to the use of cylindrical optics 15 alone and maintains the maximum interaction length.

Grating 17 is a weak transmission grating at input face 12 of crystal 10. The grating is used to seed beam fan 13 by instantaneously supplying a multiplicity of weak (seed) beams which cross input beam 11 at the optimum angle for two beam coupling for the particular crystal being used. This feature eliminates the requirement that the weak beams build up from noise (amplified scattered light). The zero order of the grating contains approximately 90% of the incident radiation and approximately 5% is present in each of the + and − orders. The gratings can either be stand alone elements or can be holographic gratings deposited directly on input face 12 of crystal 10. The first order is shown in FIG. 1 as being deposited directly on input face 12 and then amplified at the expense of the zeroth order (throughput beam). The amplified first order diffracted beam then begins to fan itself. Crystal shapes are generally parallelepipeds with face dimensions on the order of ½ to 1 cm.

Figure 2:
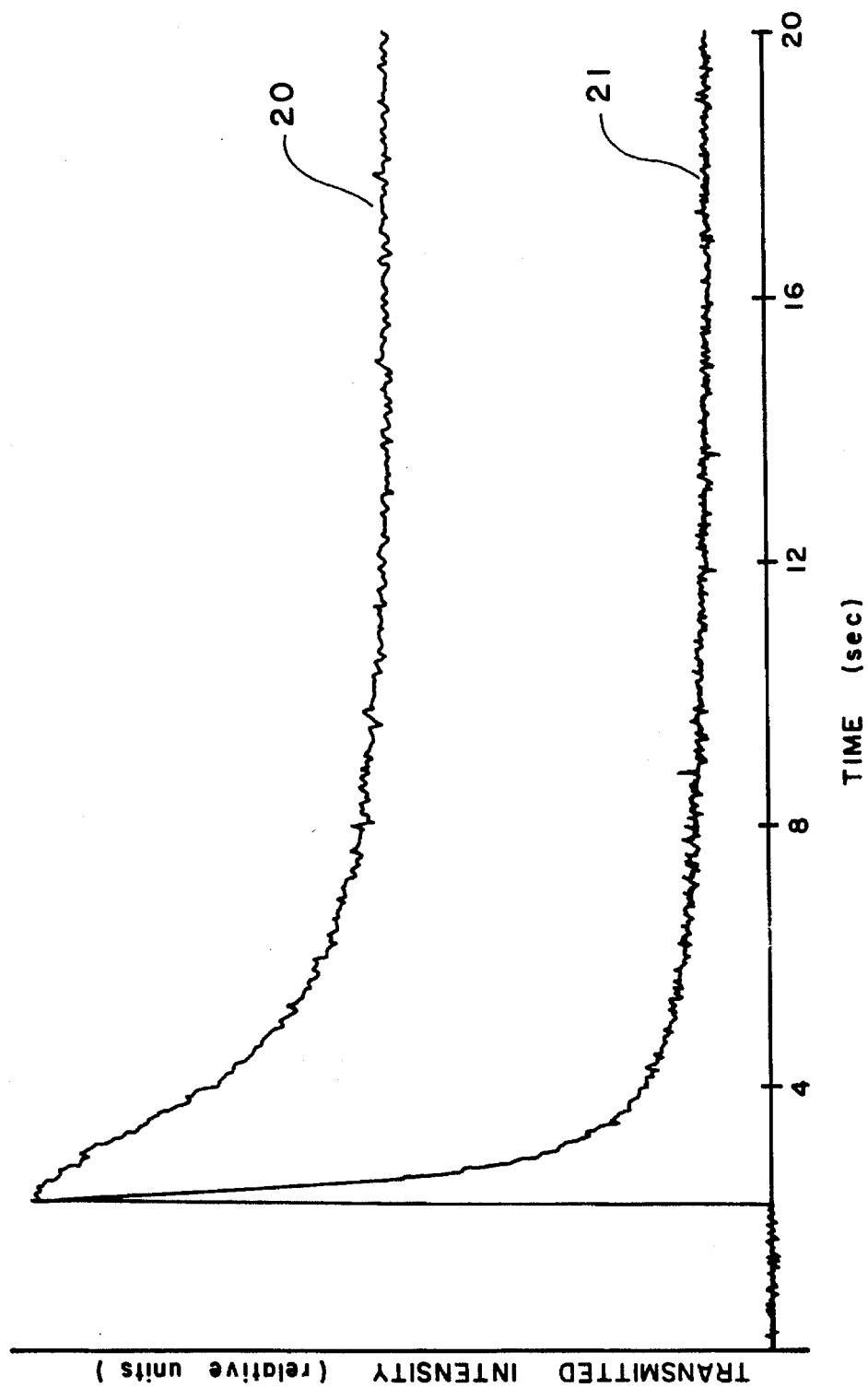
FIG. 2 is a graph of relative throughput transmission as a function of time.

FIG. 2 is a graph of relative transmission of focused input beam 16 of FIG. 1 as a function of time in seconds with and without grating 17. Line 20 and 21 show the time response curves without and with a grating respectively. The time response is improved and the lower overall transmission shows stronger beam depletion at a faster rate for line 21.

Figure 3:
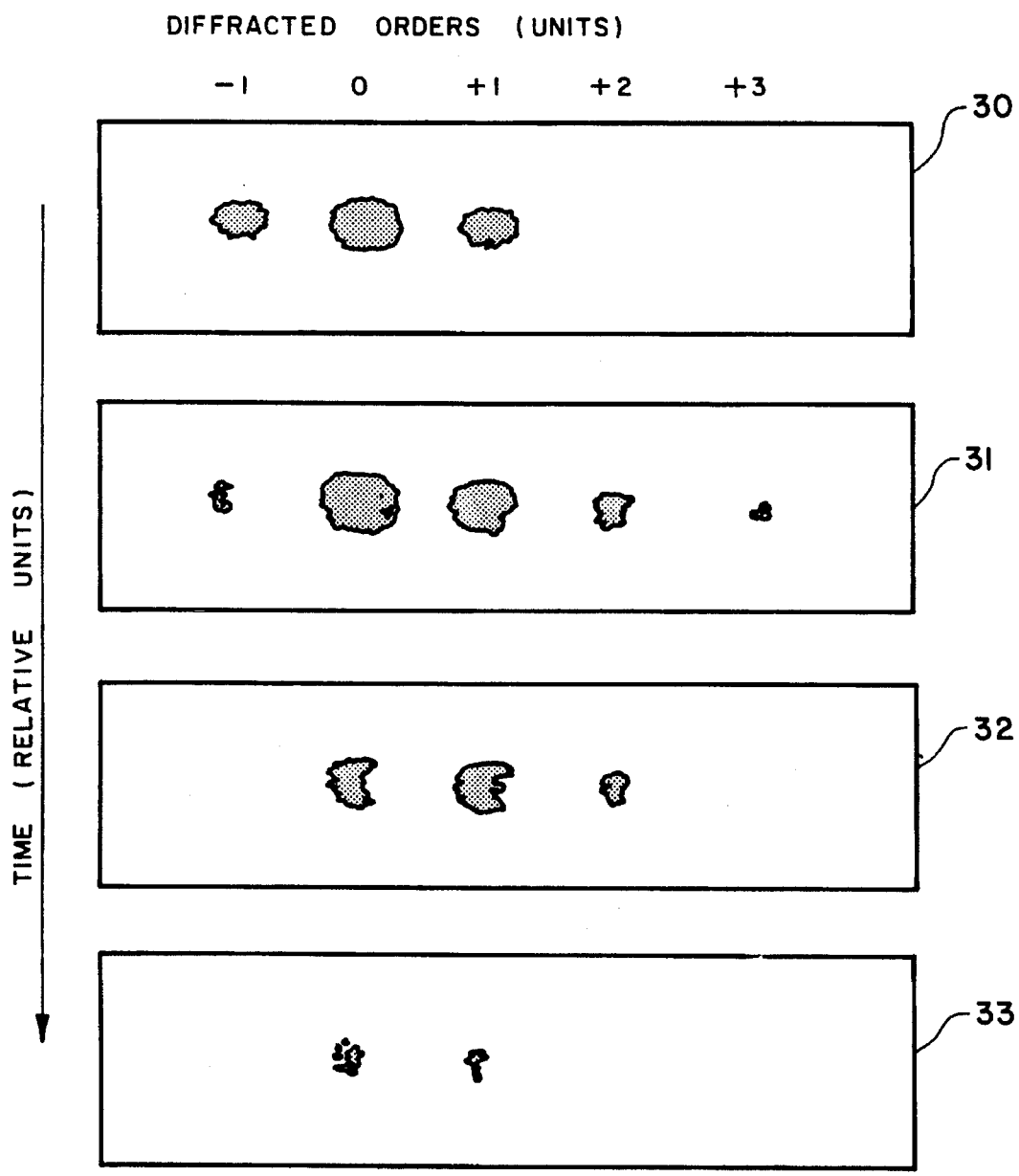
FIG. 3 is a graphical representation of beam fanning limiter output at time intervals achieved by the present invention.

FIG. 3 is a graphical representation of beam fanning limiter output at time intervals achieved by the present invention. Outputs 30 through 33 depict diffracted beam orders at increasing time intervals when grating 17 of FIG. 1 is utilized. The zeroth order is the throughput beam as shown in output 30. As time continues the −1 order begins to deplete as its energy is transferred to the zeroth order and higher positive orders. The second and third orders are now visible due to the amplification from fanning as seen in output 31. The −1 order is completely depleted as is most of the zeroth order in output 32. At steady state shown in output 33, the only light not fanned away from detector 14 of FIG. 1 is what little remains in the zeroth order.

Figure 4:
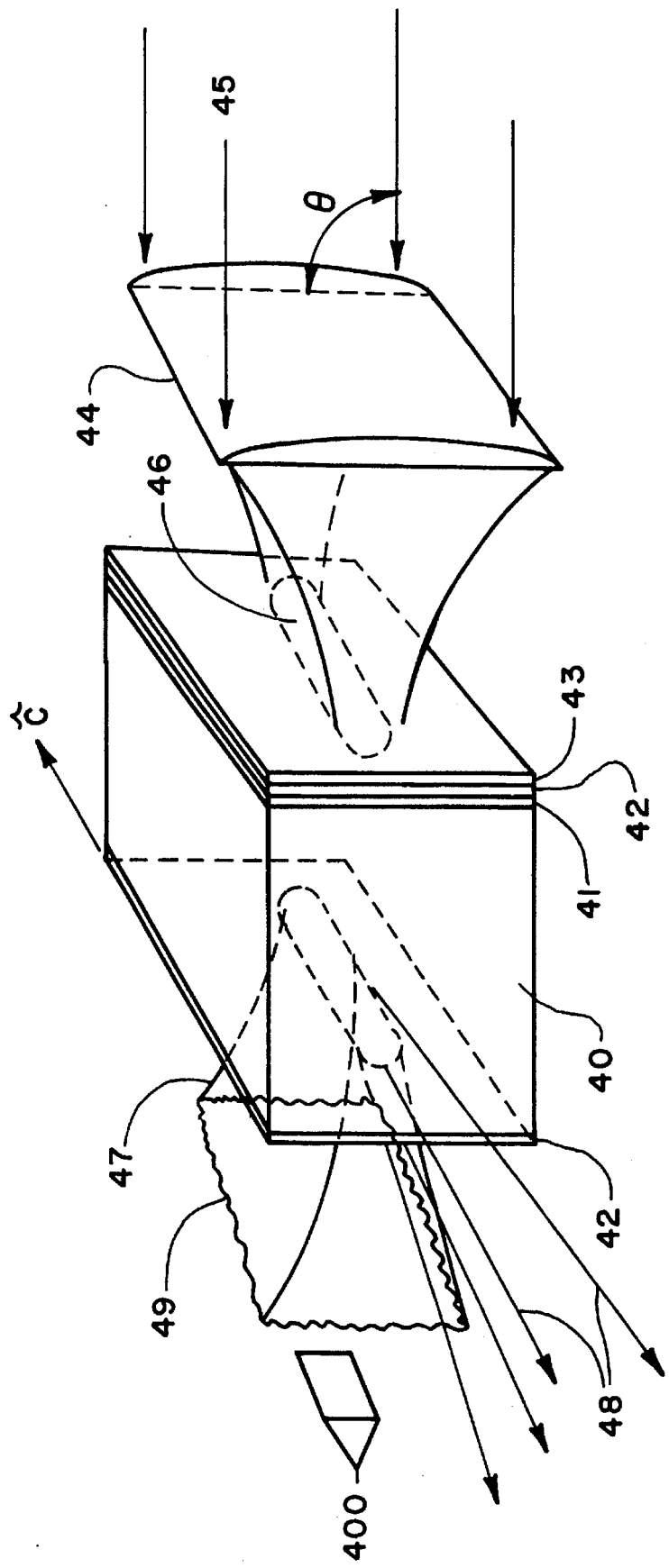
FIG. 4 is a perspective view of an anti-reflection coated crystal of strontium barium niobate (SBN), cylindrical focusing optics and a grating of the present invention.

FIG. 4 is a perspective view of an antireflection coated crystal of strontium barium niobate (SBN), cylindrical focusing optics and a grating of the present invention. The limiter device shown includes properly oriented photorefractive crystal 40, weak holographic transmission grating 41, appropriate anti-reflection coatings 42, broadband high reflectance coating 43 and cylindrical lens 44 to providing focusing of the incident radiation 45. Anti-reflection coating 42 is responsive over the range of 0.40 to 0.68 micrometers. Broadband high reflectance coating 43 reflects all radiation from 0.68 micrometers to the near infrared (NIR) spectral region, at least out to 1.5 micrometers. The beam fanning limiter is a beam control device which spatially redistributes the energy in a coherent optical beam as incident radiation 45, incident at angle 8, which may be all or a portion of the total incident radiation at the entrance aperture of the limiter. The total radiation field in the input beam is defined as that composed of both coherent laser radiation and some incoherent information bearing scene. In this embodiment shown in FIG. 4, cylindrical lens 44 focuses incident radiation 45 into intense light stripe 46 that is directed into crystal 40 so that it is coincident with the c-axis direction of crystal 40.

The geometry defined by light stripe 46 allows maximum use of the dominant electro-optic coefficients for tungsten bronze crystals and provides the maximum gain-length product for a given crystal size. In this limiting device the redistribution of energy is not a broad fan shaped distribution but is generally confined to a plane defined by the crystalline c-axis and incident stripe 46 introduced into crystal 40 by cylindrical focusing lens 44. The light exiting from crystal 40 includes transmitted beam 47 and beam fan 48 which is fanned out of the optical path in a direction determined by the direction of the crystalline c-axis, the sign of the dominant electro-optic coefficient and the sign of the charge carriers participating in the photorefractive process. When crystal 40 is rotated 90 degrees relative to the c-axis as an alternative embodiment, multi-wavelength light is also diverted from the optical path within the crystal to form a cone of intense "rainbow" of light which gives a multi-wavelength capability to the limiter device. In both embodiments, i transmitted beam 47 contains only incoherent radiation and is recorded at detector input 49 to detector 400.

A tight focus in one dimension is desired while still maintaining a long interaction length in the other to allow full exploitation of the dominant electro-optic coefficient in a particular material. The tight focus results in the desired increase in intensity of the incident laser beam and results in a much faster limiter response at no cost to the overall steady-state beam depletion. The resulting device and technique provides an improvement over photorefractive limiters without a grating resulting in improved time response, maximum use of gain-length product in the medium, and other parameters, all with a simple design. The resulting field of view for a typical f/5 system and a 1 cm cube of photorefractive material is approximately 15 degrees. The minimum reduction of incoherent light, defined as information bearing or scene light, is reduced only by a factor of 10% over the prior art. Broadband multiline protection from the entire visible spectrum is achieved for substantially all pulsewidths and continuous wave lasers. Very high optical densities of coherent light is achieved on the order of 3–4 with a high laser damage threshold on the order of 0.15 GW/cm$^2$.

The addition of a weak phase grating to seed the beam fanning process results in a reduction of time to reach steady state by an order of magnitude. Stand-alone gratings may be used such as those sold by American Holographic, Inc. They are one inch in diameter, ⅛ th inch thick discs of quartz which have holographic gratings fabricated on the surface of the disc. The grating is placed in contact with the entrance face of the photorefracted crystal. An alternative method is to deposit the holographic grating directly on the crystal face.

Figure 5:
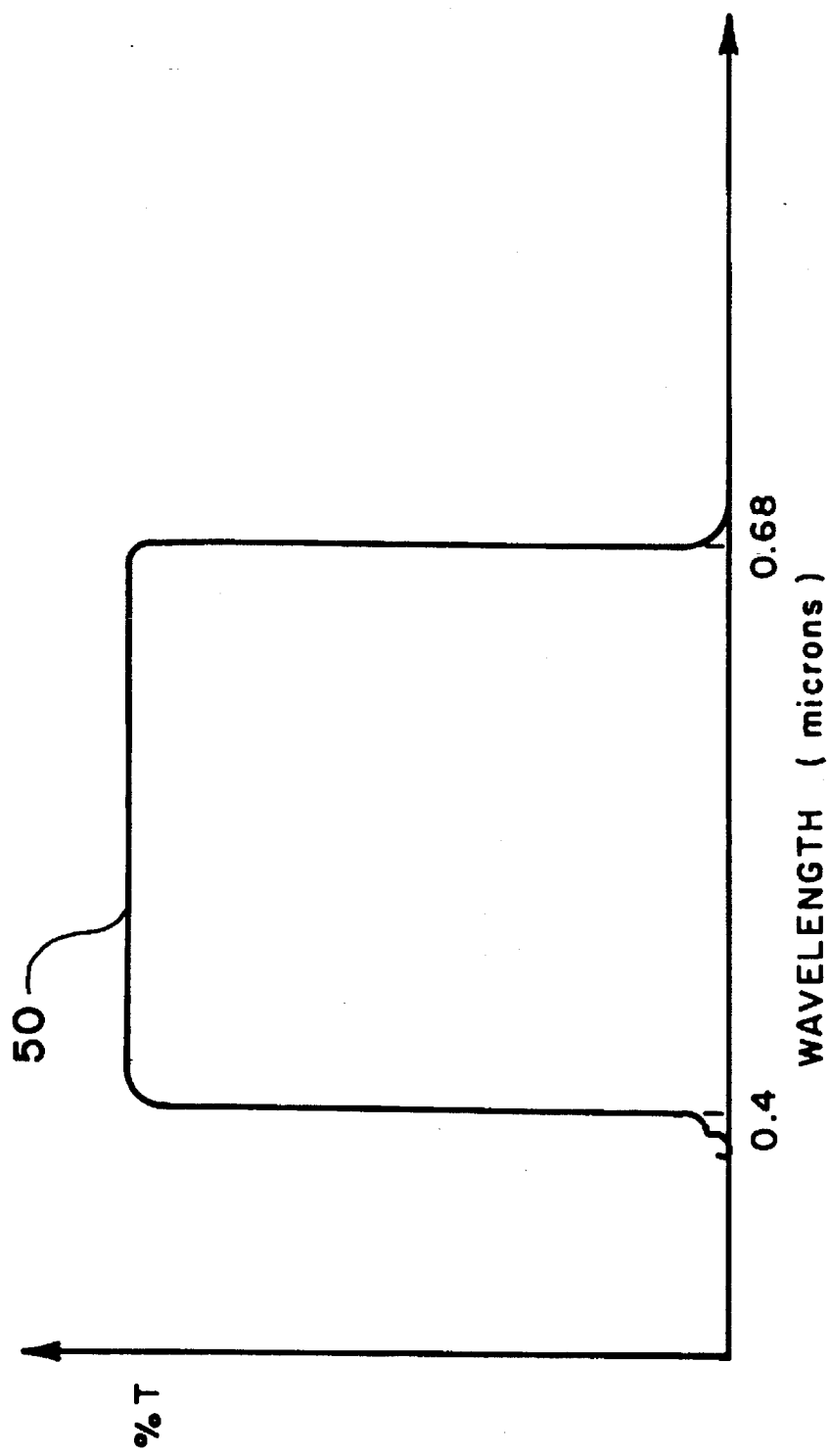
FIG. 5 is a graph of percent transmission as a function of wavelength for the arrangement shown in FIG. 4.

FIG. 5 is a graph of percent transmission as a function of wavelength for the generalized transmission characteristics of coatings 42 and 43 of FIG. 4 utilizing a typical 1 cm thick specimen of SBN, BSKNN or BaTiO$_3$ for incoherent radiation. The transmission of coherent light in this incoherent spectral "pass band" shown as band 50 is strongly attenuated due to beam fanning. Since the linear absorption of these photorefractive materials can be very low the device will have low insertion loss for incoherent light and provide very fast strong attenuation of coherent light.

While this invention has been described in terms of preferred embodiment consisting of the fast broadband optical limiter technique and device, those skilled in the art will recognize that the invention can be practiced with modification within the spirit and scope of the appended claims.

Having thus described my invention, what We claim as new and desire to secure by Letters Patent is as follows:

1. A passive broadband sensor protection and enhancement system which achieves broadband multiline protection from the visible spectrum for substantially all pulsewidths and continuous wave lasers, with enhanced time response and interaction length, the system including:
- a cylindrical lens on an optical axis which focuses incident light into an intense light strip;
- a photorefractive crystal on the optical axis, the crystal including an input and output face, where the intense light strip is coincident upon the input face relative to a plane normally referred to as the c-axis of the crystal;
- a broadband high reflect ion coating proximate to the input face for reflection of all radiation from approximately 0.68 to at least out to 1.5 micrometers wavelength;
- a weak holographic transmission grating proximate to the input face, whereby light exiting from the output face of the crystal results from a photorefractive process that includes a transmitted beam and beam fan, where the grating is used to seed the beam fan by instantaneously supplying a multiplicity of weak beams which cross the input beam at an optimum angle for two beam coupling for the crystal being used, such that the transmitted beam contains only incoherent radiation as input to detector resulting in broadband multiline protection from the visible spectrum for substantially all pulsewidths and continuous wave lasers, with enhanced time response and interaction length.

2. The passive broadband sensor protection and enhancement system of claim 1 wherein there is further included an anti-reflection coating proximate to the input and output faces of the photorefractive crystal responsive over approximately a 0.40 to 0.68 micrometer wavelength range.

3. A passive broadband sensor protection and enhancement technique which achieves broadband multiline protection from the visible spectrum for substantially all pulsewidths and continuous wave lasers, with enhanced time response and interaction length, the technique including the steps of:
- providing a photorefractive crystal on the optical axis, the crystal including an input and output face;
- providing for reflection of all input radiation proximate to the input face, from approximately 0.68 to at least out to 1.5 micrometers wavelength;
- providing a weak holographic transmission grating also proximate to the input face;
- focusing incident light on the optical axis into an intense light strip coincident upon the input face relative to a plane normally referred to as the c-axis of the crystal, whereby light exiting from the output face of the crystal results from a photorefractive process that includes a transmitted beam and beam fan, the beam fan is fanned out of the optical path where the grating provided is used to seed the beam fan by instantaneously supplying a multiplicity of weak beams which cross the input beam at an optimum angle for two beam coupling for the crystal being used, such that the transmitted beam contains only incoherent radiation as input to a detector resulting in broadband multiline protection from the visible spectrum for substantially all pulsewidths and continuous wave lasers, with enhanced time response and interaction length.

4. The passive broadband sensor protection and enhancement technique of claim 3 wherein their is further provided an antireflection coating proximate to the input and output faces of the photorefractive crystal responsive over approximately a 0.40 to 0.68 micrometer wavelength range.

* * * * *